US011241189B2

(12) United States Patent
Smiley et al.

(10) Patent No.: US 11,241,189 B2
(45) Date of Patent: Feb. 8, 2022

(54) WIRELESS BOWEL SENSOR

(71) Applicants: THE CLEVELAND CLINIC FOUNDATION, Cleveland, OH (US); The United States Government as represented by the Department of Veterans Affairs, Washington, DC (US); The MetroHealth System, Cleveland, OH (US)

(72) Inventors: Aref Smiley, Cleveland, OH (US); Dennis Bourbeau, Cleveland Hts., OH (US); Margot S. Damaser, Cleveland Hts., OH (US); Steve Majerus, University Hts., OH (US); Massarat Zutshi, Cleveland Hts., OH (US); Ian Mcadams, Cleveland Hts., OH (US)

(73) Assignees: THE CLEVELAND CLINIC FOUNDATION, Cleveland, OH (US); THE METROHEALTH SYSTEM, Cleveland, OH (US); THE U.S. GOV'T AS REPRESENTED BY THE DEPT OF VETERANS AFFAIRS, Washington, DC (US)

( * ) Notice: Subject to any disclaimer, the term of this patent is extended or adjusted under 35 U.S.C. 154(b) by 372 days.

(21) Appl. No.: 16/514,982

(22) Filed: Jul. 17, 2019

(65) Prior Publication Data
US 2020/0022642 A1 Jan. 23, 2020

Related U.S. Application Data

(60) Provisional application No. 62/700,971, filed on Jul. 20, 2018.

(51) Int. Cl.
*A61B 5/07* (2006.01)
*A61B 5/00* (2006.01)
*A61N 1/36* (2006.01)

(52) U.S. Cl.
CPC .......... *A61B 5/4255* (2013.01); *A61B 5/0031* (2013.01); *A61B 5/07* (2013.01); *A61N 1/36007* (2013.01); *A61B 5/0022* (2013.01)

(58) Field of Classification Search
CPC ......... A61B 5/00; A61B 5/145; A61B 5/1473; A61B 5/14735; A61B 5/6861;
(Continued)

(56) References Cited

U.S. PATENT DOCUMENTS 5,247,938 A * 9/1993 Silverstein ............. A61B 1/018
600/459
7,192,397 B2 3/2007 Lewkowicz et al.
(Continued)

FOREIGN PATENT DOCUMENTS

WO 2005/062717 A3 7/2005

OTHER PUBLICATIONS

Lo YK, Wang PM, Dubrovsky G, et al. A Wireless Implant for Gastrointestinal Motility Disorders. Micromachines (Basel). 2018;9(1): 17. Published Jan. 2, 2018. doi:10.3390/mi9010017 (Year: 2018).*
(Continued)

*Primary Examiner* — Eric J Messersmith
(74) *Attorney, Agent, or Firm* — Tarolli, Sundheim, Covell & Tummino LLP

(57) ABSTRACT

A sensing device can be placed within the colon to study bowel function. The sensing device can include a flexible printed circuit board that includes at least one senor configured to record data related to bowel activity from a patient's colon; and a wireless transmitter configured to send the data from the patient's colon to an external device. The sensing device can also include at least one mucosal clip configured to fix the sensor board to a wall of the patient's colon for a measurement period. The flexible printed circuit board and/or the at least one mucosal clip are configured to be passed
(Continued)

from the patient's colon after the measurement period through normal defecation.

11 Claims, 11 Drawing Sheets

(58) Field of Classification Search
CPC .............. A61B 5/14507; A61B 5/4866; A61B 5/14539; A61B 2562/0295
See application file for complete search history.

(56) References Cited

U.S. PATENT DOCUMENTS

| | | | |
|---|---|---|---|
| 7,708,705 | B2 | 5/2010 | Iddan et al. |
| 7,756,582 | B2* | 7/2010 | Imran .................. A61F 5/0003 607/40 |
| 7,970,455 | B2 | 6/2011 | Zilberstein et al. |
| 9,227,011 | B2 | 1/2016 | Shimizu et al. |
| 2017/0027520 | A1* | 2/2017 | Terry ................. A61B 10/0283 |
| 2019/0216384 | A1* | 7/2019 | Duval .................... A61B 7/008 |

OTHER PUBLICATIONS

Tran, Khoa, Rita Brun, and Braden Kuo. "Evaluation of regional and whole gut motility using the wireless motility capsule: relevance in clinical practice." Therapeutic advances in gastroenterology 5.4 (2012): 249-260.
Quan, Xiaojing, et al. "Relationships between motor patterns and intraluminal pressure in the 3-taeniated proximal colon of the rabbit." Scientific reports 7 (2017): 42293.
Maqbool, Sabba, Henry P. Parkman, and Frank K. Friedenberg. "Wireless capsule motility: comparison of the SmartPill® GI monitoring system with scintigraphy for measuring whole gut transit." Digestive diseases and sciences 54.10 (2009): 2167-2174.
Chen, Ji-Hong, et al. "Intraluminal pressure patterns in the human colon assessed by high-resolution manometry." Scientific reports 7 (2017): 41436.

* cited by examiner

WIRELESS BOWEL SENSOR

CROSS-REFERENCE TO RELATED APPLICATIONS

This application claims the benefit of U.S. Provisional Application No. 62/700,971, filed Jul. 20, 2018, entitled "WIRELESS BOWEL SENSOR". This provisional application is hereby incorporated by reference in its entirety for all purposes.

GOVERNMENT FUNDING

This invention was made with government support, grant no. OT2OD023873 awarded by the National Institutes of Health. The government has certain rights in the invention.

TECHNICAL FIELD

The present disclosure relates generally to bowel function and, more specifically, to a sensing device that can be used to make continuous measurements of data related to bowel function and send the data to an external device.

BACKGROUND

Bowel function during storage and emptying is poorly understood, including the coordination between colon, rectum, and anal activity and the neural mechanisms underlying control of these structures. Several methods have been developed to diagnose bowel dysfunction clinically and have been used for research studies to understand the neural control of bowel function, including: passing objects through the alimentary canal, pressure manometry using fluid-filled balloons inserted into the rectum; and anal electromyogram. However, these approaches have practical limitations such as cost, failing to provide continuous measurement of bowel function, inconvenience, discomfort, and impracticability for use during normal daily activities, making these approaches insufficient for chronic, ambulatory sensing of bowel fullness, and activity. While the neural control of the bowel can be determined using existing methods, such as implantable or percutaneous real-time neural recording devices, it is difficult to elucidate cause and effect of bowel motility from neural recordings without simultaneous and continuous measurement of bowel function and activity.

SUMMARY

The present disclosure relates to a sensing device that can be used to make continuous measurements of data related to bowel function and send the data to an external device.

In an aspect, the present disclosure describes a sensing device. The sensing device includes a flexible printed circuit board and at least one mucosal clip. The flexible printed circuit board includes at least once sensor configured to record data related to bowel activity from a patient's colon. The flexible printed circuit board further includes a wireless transmitter configured to send date from the patient's colon to an external device. The sensing device's at least one mucosal clip is configured to fix the sensor board to a wall of the patient's colon for the duration of a measurement period. The flexible printed circuit board and/or the at least one mucosal clip are further configured to be passed from the patient's colon after the measurement period through normal defecation.

In another aspect, the present disclosure further describes a method for measuring and collecting data related to bowel activity from a patient's colon during a measurement period. The method includes recording data related to bowel activity from the patient's colon during a measurement period by using at least one sensor located on a flexible printed circuit board of a sensing device anchored to a patient's colon by at least one mucosal clip. The method further includes sending the data from the patient's colon to an external device during the measurement period by using a wireless transmitter of the sensing device. The method also includes the patient passing the printed circuit board and/or the at least one mucosal clip from the patient's colon through normal defecation after the end of the measurement period.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
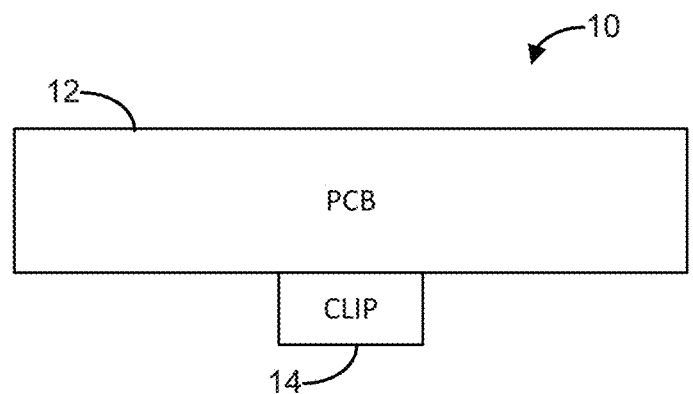
FIGS. 1 and 2 illustrate diagrams of example sensing devices that can be used to make continuous measurements of data related to bowel function and send the data to an external device, according to an aspect of the present disclosure.

In the context of the present disclosure, the singular forms "a," "an" and "the" can also include the plural forms, unless the context clearly indicates otherwise.

As used herein, the terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the terms "colon" and "bowel" are used interchangeably throughout and refer to a patient's large intestine (in its entirely or as a portion thereof—e.g., the cecum, the ascending colon, the transverse colon, the descending colon, or the sigmoid portion) and/or the rectum.

As used herein, the term "sensing device" can refer to any device configured for implantation within a patient's colon with one or more components (e.g., sensors and/or transducers) that detect or measure one or more physical properties of the patient's colon. In some instances, the sensing device can include one or more components (e.g., a battery or power source, a controller or other processor, a wireless transmitter or transceiver, etc.) that record, indicate, or otherwise respond to the one or more physical properties of the patient's colon. In some instances, the sensing device can include a printed circuit board, which may be flexible, to house electronic components (e.g., sensors/transducers, controller, battery, wireless transceiver, etc.) and an attachment mechanism (e.g., a mucosal clip) to anchor the printed circuit board within the colon.

As used herein, the term "physical properties of the patient's colon" relate to information that can be sensed or interpreted based on sensed information. For example, the sensing device can include a pressure sensor, a volume sensor, a conductance sensor, or the like, and the physical properties of the patient's colon can include a volume of the bowel, an aspect ratio of bowel contents, a shape of bowel contents, a geometry of bowel contents, a movement of bowel contents, a motility of bowel content, a material content of bowel content, a material form of bowel content, a pressure of bowel content, bowel circumference, or the like.

As used herein, the term "printed circuit board" can refer to something that mechanically supports and electrically connects electronic components using conductive tracks, pads, and other features etched from one or more sheet layers of a conductor (e.g., copper) laminated onto and/or between sheet layers of a non-conductive substrate.

As used herein, the term "flexible" printed circuit board can refer to a printed circuit board that can be manipulated (e.g., in X, Y, and/or Z directions). In some instances, a flexible printed circuit board can be manipulated in at least one direction. In other instances, a flexible printed circuit board can be manipulated in at least two directions. In still other instances, a flexible printed circuit board can be manipulated in at least three directions.

As used herein, the term "mucosal clip" can refer to a clamp-based attachment mechanism used to close two mucosal surfaces (e.g., two surfaces on the interior of the colon).

As used herein, the term "in vivo" can refer to a process being performed or taking place inside a living organism.

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to detection of data related to bowel function (e.g., to aid in the diagnosis of bowel dysfunction). Diagnosis of bowel dysfunction is difficult as the bowel is an autonomic organ. This results in symptoms of dysfunction often being diffuse and nonspecific. Several methods have been developed to diagnose bowel dysfunction clinically and these methods are currently being used for research studies to understand the neural control of bowel function. These methods include passing objects through the alimentary canal, such as fluoroscopic markers or the Smart Pill; pressure manometry using fluid-filled balloons inserted into the rectum; and anal electromyogram. These approaches are informative but have practical limitations. Swallowing markers does not provide continuous measurement of bowel function and can be costly and inconvenient. Pressure manometry may be physically uncomfortable and impractical for use during normal daily activities. Thus, they are insufficient for chronic, ambulatory sensing of bowel fullness and activity. Diagnosis is further complicated by wired/tethered instrumentation, such as catheters, and imaging methods that require radiation exposure. Newer technologies such as the Smart Pill travel through the alimentary canal, so it can be difficult to identify which part of the GI system data recorded using the newer technologies comes from.

The present disclosure describes a new type of sensing device that can aid in the diagnosis of bowel dysfunction in a manner that is less expensive, less uncomfortable, less impractical and longer lasting compared to previous solutions. The sensing device described herein employs wireless, catheter-free technology to enable monitoring of bowel function via high fidelity data recorded from a single location in the bowel for a measurement period (e.g., several days-several weeks). This data will enable individualized therapy for bowel disorders such as fecal incontinence, constipation, inflammatory bowel disorders, Crohn's disease, and other pathologies. In addition, this data can be utilized to obtain objective data regarding the efficacy of treatments, enabling individualized therapy and development of improved therapies. After the measurement period, the sensing device can be passed in a bowel movement and then can be discarded. The sensing device is designed to be biomimetic, following the form of intestinal parasites that grip the intestinal mucosa and maintain their position for a long time.

III. Systems

Figure 2:
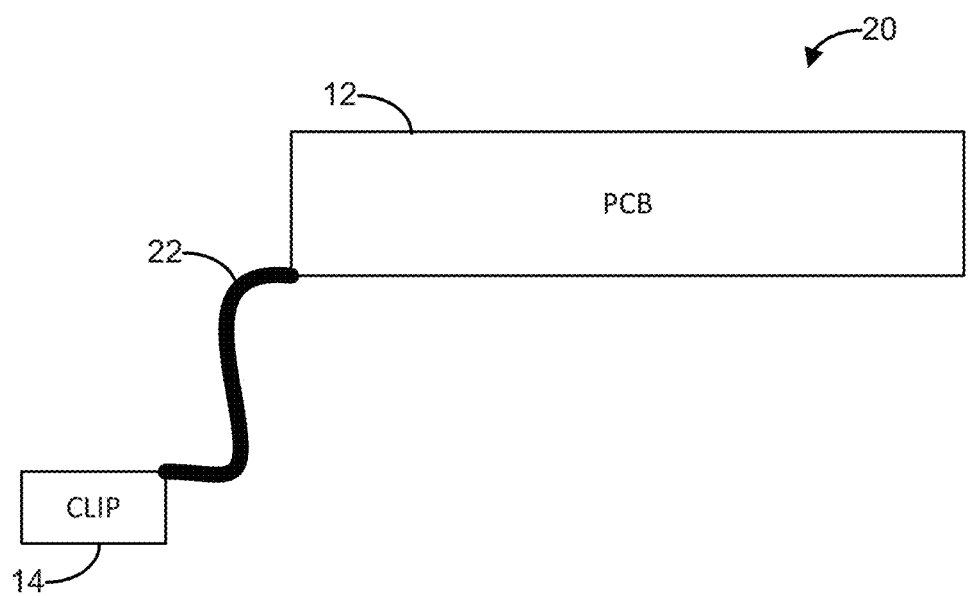

FIGS. 1 and 2 together illustrate a sensing device 10 and 20 that can be placed within a patient's colon and used to make continuous measurements of data related to bowel function and send the data to an external device. The sensing device 10 and 20 can be used in the continuous measurement of bowel state and activity, while being less expensive, less uncomfortable, less impractical and longer lasting compared to previous solutions.

The sensing device 10 shown in FIG. 1 includes a flexible printed circuit board (PCB) 12 and a clip 14 that is designed to anchor the flexible PCB 12 within a patient's colon during a measurement period (and can dislodge the flexible PCB 12 from the colon after the measurement period). After the measurement period, the flexible PCB 12 and/or the clip 14 can be passed from the patient's colon through normal defecation. Although the clip 14 is located in FIG. 1 in the middle of the flexible PCB 12, the clip 14 can be located in any position relative to the flexible PCB 12. Moreover, the flexible PCB 12 can be connected to more than just one clip 14. The clip 14 can be, for example, a mucosal clip. Additionally, in some instances, the sensing device can include a u-shaped handle that can be used to attach the clip 14 to the colon wall (and subsequently removed from the colon). As shown in FIG. 2, for example, the clip 14 need not be directly contacting the flexible PCB 12. Instead, the flexible PCB 12 can include an extending portion 22 that extends from the flexible PCB 12 to the clip 14.

The flexible PCB 12 can include at least one sensor and a wireless transceiver. The at least one sensor can be configured to record data related to bowel activity from a patient's colon. For example, the data can be used to determine one or more physical properties of the patient's colon. The physical properties of the patient's colon can include a volume of the bowel, an aspect ratio of bowel contents, a shape of bowel contents, a geometry of bowel contents, a movement of bowel contents, a motility of bowel content, a material content of bowel content, a material form of bowel content, a pressure of bowel content, bowel circumference, or the like. As an example, the at least one sensor can include a pressure sensor, a conductance sensor, and/or a capacitance sensor. The pressure sensor can be located at a head of the flexible PCB 12 (see FIG. 5). The pressure sensor can be used to detect contraction of circular smooth muscle in the bowel. Metal mesh electrodes of the conductance sensor and/or the capacitance sensor are located at a tail of the flexible PCB 12 (see FIG. 5—an anode A and three cathodes C1, C2, C3 located at different distances from one another).

The wireless transceiver can be configured to send data from the patient's colon to an external device. The flexible PCB 12, in some instances, can include additional components, like a controller (e.g., a microcontroller) or other type of processor, a battery or other type of power source, or the like. The controller can be used to perform calculations related to the recorded data (e.g., to determine the physical properties).

IV. Methods

Figure 3:
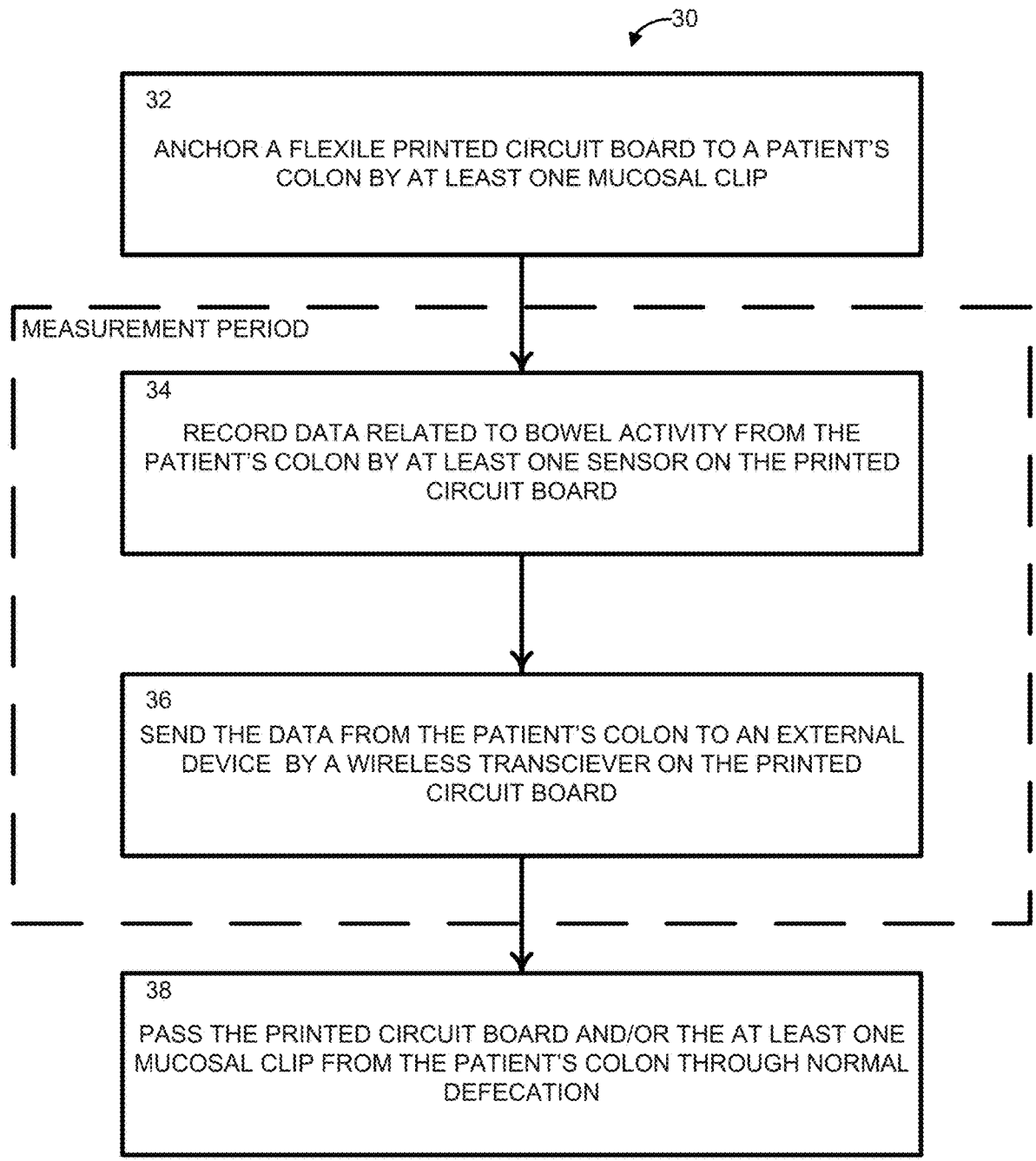
FIG. 3 illustrates a method for making continuous measurements of data related to bowel function and sending the data to an external device, according to another aspect of the present disclosure.

Another aspect of the present disclosure includes a method 30 shown in FIG. 3, which can contribute to improved detection of bowel function. For purposes of simplicity, the method 30 is shown and described as being executed serially; however, it is to be understood that the present disclosure is not limited by the illustrated order as some steps could occur in different orders and/or concurrently with other steps shown and described herein. Moreover, not all illustrated aspects may be required to implement the method 30.

Figure 5:
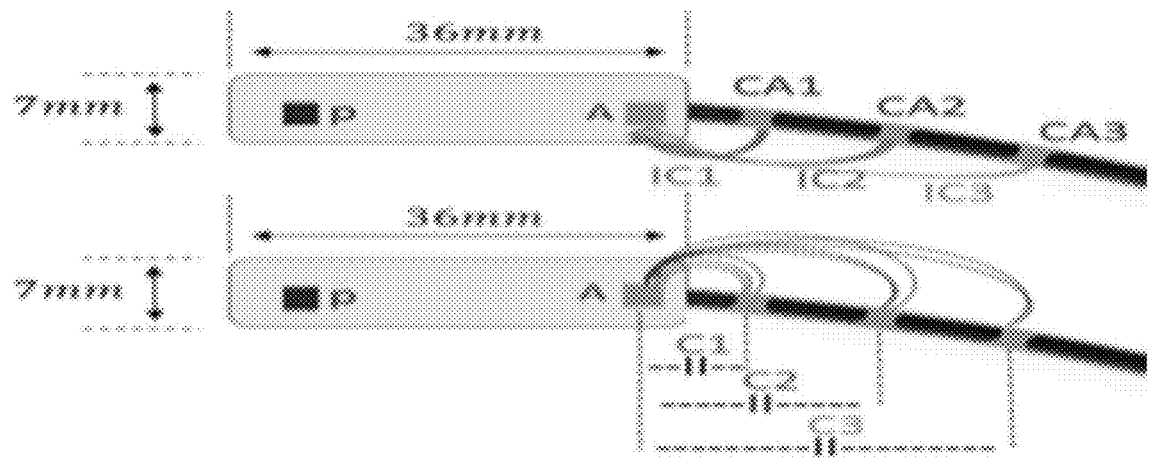
FIG. 5 illustrates a diagram of three cathodes (CA1, CA2, and CA3) and one anode (A), which are used as conductance and capacitive sensors (C1, C2, and C3). The differing electrode spacings enable detection of stool volume change.

The method 30 includes three distinct stages—before measurement (including at least step 32), during a measurement period (including at least steps 34 and 36), and after the measurement period (including at least step 38). At step 32, before measurement, a flexible printed circuit board can be anchored to a patient's colon (e.g., by at least one mucosal clip). The flexible printed circuit board can include one or more sensors, such as a pressure sensor, a volume sensor, a conductance sensor, or the like. An example type of flexible printed circuit board is shown in FIG. 5, with a pressure sensor at one end of the flexible printed circuit board and an anode (A) on the other end with three cathodes (CA 1-3) on the other end (serving as a volume or conductance/capacitance sensor).

After the flexible printed circuit board is anchored, the measurement period can begin. The measurement period can last for at least 48 hours, for example. However, the measurement period may last for days, weeks or months depending on patient needs. At step 34, data can be recorded related to bowel activity from the patient's colon by at least one sensor on the flexible printed circuit board. For example, the data can be used to determine one or more physical properties of the patient's colon. The physical properties of the patient's colon can include a volume of the bowel, an aspect ratio of bowel contents, a shape of bowel contents, a geometry of bowel contents, a movement of bowel contents, a motility of bowel content, a material content of bowel content, a material form of bowel content, a pressure of bowel content, bowel circumference, or the like. At step 36, the data can be sent to an external device by a wireless transmitter of the sensing device (e.g., located on the flexible printed circuit board).

After expiry of the measurement period, at step 38, the flexible printed circuit board and/or the at least one mucosal clip can be passed from the patient's colon through normal defecation. In some instances, the at least one mucosal clip can dissolve during or after the measurement period to allow the flexible printed circuit board to de-anchor from the colon and be passed from the patient's colon through normal defecation.

V. Experimental

The following description of example experiments is shown for the purpose of illustration only and is not intended to limit the scope of the appended claims. These example experiments show the selection and validation of example sensing devices.

Methods
Sensor Selection and Benchtop Validation
A. Sensor Types and Sensing Modalities The colon and rectum move stools by coordinated contractions of circular and longitudinal smooth muscles. The goal was to measure the fullness, activity, and motility of a section of colon. A set of promising sensor modalities was identified (Table 1) to measure colon fullness (volume), colon activity (contractions), and colon motility (movement of contents). The pressure sensor was designed to detect contraction of circular smooth muscle in the bowel. By monitoring multiple sensors at different locations, peristalsis can be detected. Infrared (IR) sensing was expected to measure the distance between the sensor and colon wall or stool, providing an estimate of bowel fullness.

TABLE I

BOWEL SENSORS EVALUATED IN THIS STUDY.

| Sensing Method | Fullness | Activity | Motility | Size (mm) |
|---|---|---|---|---|
| Pressure [7] |  | ✓ | ✓ | 2 × 2 × 0.76 |
| Infrared [8] | ✓ |  |  | 2.7 × 3.4 × 1.6 |
| Color [9] | ✓ |  |  | 2 × 2.4 × 0.6 |
| Conductivity | ✓ | ✓ | ✓ | ~20-30 long |
| Capacitance | ✓ | ✓ | ✓ | ~20-30 long |

The color sensor was expected to discern the empty pink colon from brown or green stools. Conductivity and capacitive sensors were expected to measure volume changes of the stool at the sensor location. Increasing or decreasing the volume of stool would be expected to change the resistivity or dielectric effect. Benchtop and in vivo testing results confirmed the best practical choices to be later considered Two important factors in sensor selection for a wireless implanted device are size and power consumption. Since the final device is expected to be inserted and fixed inside the colon, it should be small enough to easily pass through the rectum and colon and not obstruct the colon during normal physiological function. Measurements of pig colons revealed that the average colon diameter was approximately 3-5 cm. Since the final sensors will communicate wirelessly with an external portable transceiver for at least 48 hours, they should be capable of functioning at low power.

B. Sensor Functional Testing and Selection

Figure 4:
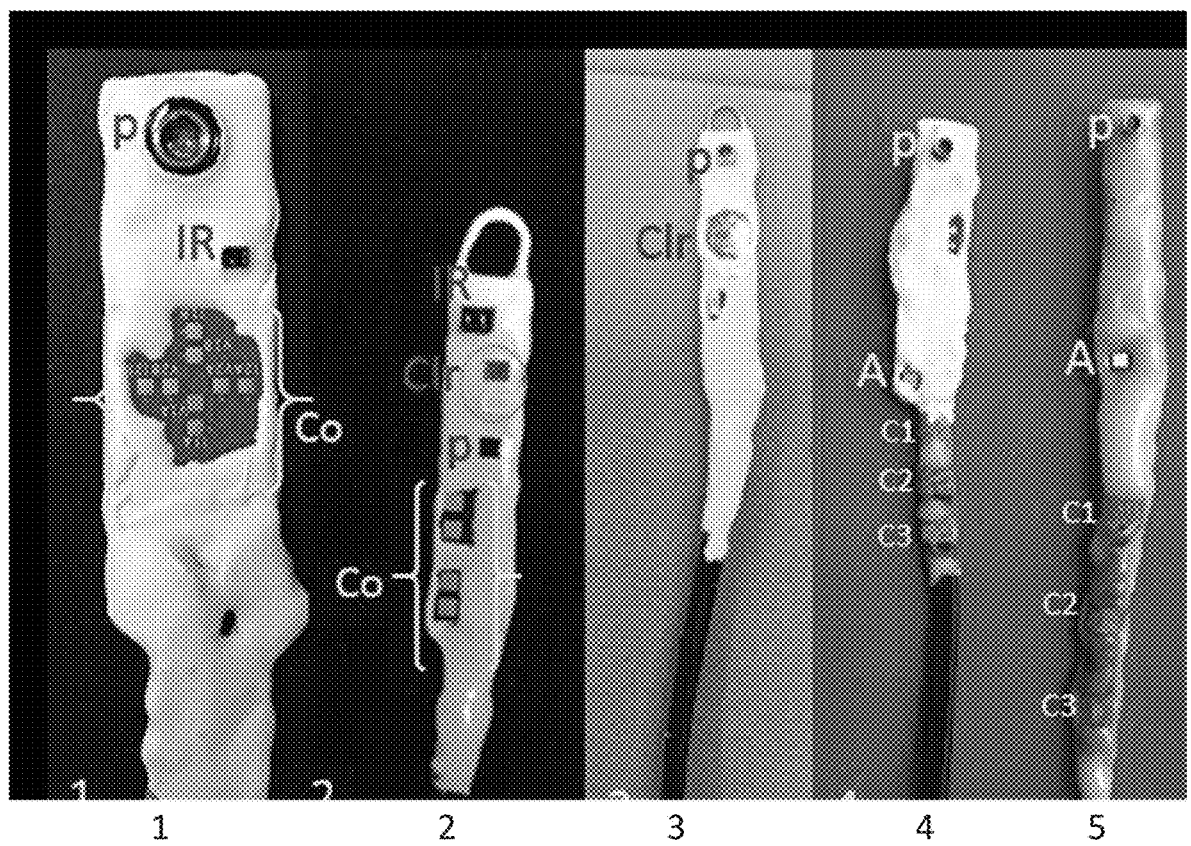
FIG. 4 illustrates prototype bowel sensor designs (prototypes 1-5) based on results from benchtop and in vivo experiments. #1 shows the initial fabricated prototype, and #2 shows a smaller design with a u-shaped handle to attach the mucosal clip to the colon wall. Boards 1, 2, and 3 tested four types of sensors: Pressure (P), infrared (IR), Color (Clr), and conductivity (Co), with Clr coated in clear epoxy in #3. #4 is the most updated sensor board, with P, one anode (A) and three cathodes (C1, C2, C3) for both conductivity and capacitance measurements.

Sensors were mounted to small, wired test boards and encapsulated to be waterproof for benchtop and in vivo testing (FIG. 4). The first fabricated board was approximately 20 mm×50 mm with pressure and IR sensors as well as 8 electrodes for conductivity measurements in two dimensions (FIG. 4, device 1). The board was modified with a smaller pressure sensor (P), a color sensor (Clr), and conductivity measurements along a single axis (FIG. 4, device 2). During initial in vivo testing, it was discovered that as soon as Clr and IR sensors were coated by stool, they would not detect further changes in stool volume. A thick window of clear epoxy was incorporated above the color sensor and its nearby LED to attempt to resolve the issue (FIG. 4, device 3). However, in further in vivo testing, this design did not provide significant improvements in sensor function The most recent design iteration comprised a miniaturized PCB (7 mm×36 mm) with three sensor modalities, including pressure, conductivity, and capacitive sensors (FIG. 4, device 4). Overall, this design was based on two major concepts: (1) measurement of pressure, which can detect peristalsis and the level of pressure inside the colon or rectum; and (2) conductivity and capacitive measurements, which provide information about the presence and volume of stools surrounding the sensor.

Conductive and capacitive sensors can differentiate between the state and type of the substances by recording changes in either resistivity or the dielectric effects of substances. Such changes could be because of the stool volume change or attachment of the colon wall to the sensor (empty colon). Therefore, the combination of pressure, conductivity, and capacitive sensors will provide useful information about the state and activity of the colon in addition to the type and volume of the substances. Importantly, these simple sensor modalities are easily implemented in low-power hardware and at small scales.

C. Fabrication of Multi-Mode Sensor Platform

A sensor board was designed to include only pressure, conductivity, and capacitive sensors (FIG. 4, device 4). The pressure sensor was located at the head of the PCB and the metal mesh electrodes for conductivity and capacitive sensors were located at the tail of the device. The pressure sensor was protected from the aqueous environment by coating it in dielectric silicone gel. Each prototype consisted of four electrodes (three cathodes (CA1, CA2, CA3) and one anode (A)) located at different distances from each other (FIG. 5). The electrodes were made of 316 alloy stainless steel mesh which has robust corrosion resistance properties. Coated stainless steel wires were soldered to the electrodes to enable measurement. These electrodes were also used to form the plates for capacitive measurements (FIG. 5). Capacitance is determined in this device through RC decay time measurement, which is easily measured by microcontrollers in a time-to-digital coding. Stool volume change could result in the dielectric change and therefore RC decay change. For conductivity, the three transmitting electrodes drive electrical current into the stool while the common anode (A) measures the voltage drop due to the stool. Therefore, the stool would either change the dielectric effect or resistivity.

The PCB and the solder joints of the electrodes were coated by epoxy for insertion into the pig colon for acute in vivo testing. The only exposed sections of the device were the pressure sensor head (protected with gel) and the electrodes. Finally, a U-shape handle was placed at the head of the PCB to be used for the attachment of the device to the colon wall using mucosal clips (FIG. 4, device 2).

D. Prototype Sensor Bench Test and Calibration

Figure 6:
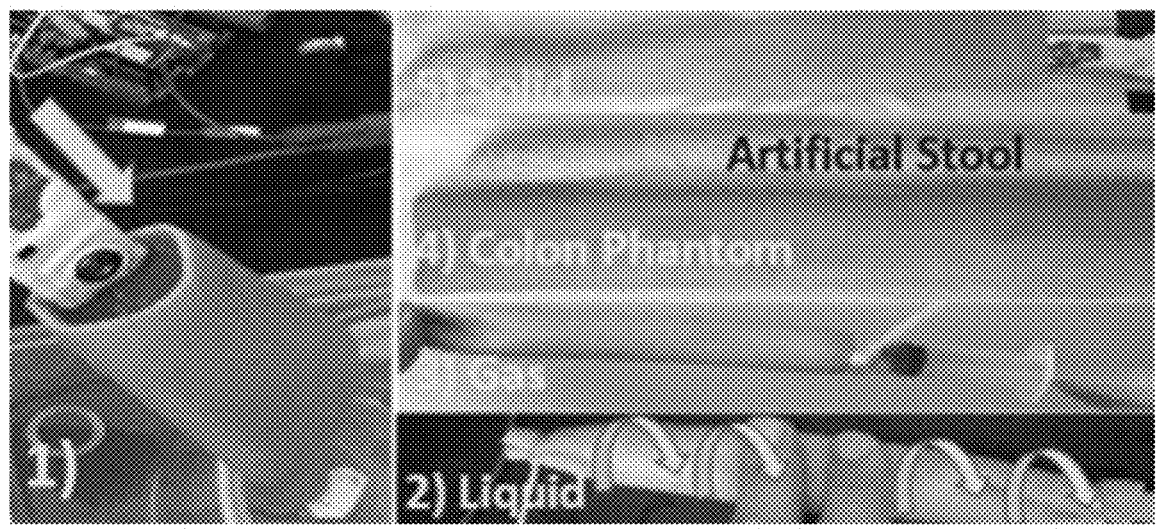
FIG. 6 is a photograph of a benchtop test phantom. Sensor boards were tested in three conditions: solid, liquid, and gas. The board was inserted in the phantom (#1) and the phantom was filled with liquid (#2) or gas (#3). For solids, sensors were tested by passing artificial stool through the phantom over the sensor board (#4 & 5.

To test and calibrate the sensors prior to in vivo use, the prototype device responses to pressure, infrared (IR), color, conductivity and capacitive measurements were characterized through benchtop testing in a colon phantom (FIG. 6). To simulate the environment of a colon on the bench, the prototypes from FIG. 4 were inserted into a silicone phantom (3.5 cm diameter) while it was filled with liquid, gas, or solid materials (FIG. 6).

E. Animal Preparation

A total of 3 acute in vivo experiments were performed in male and female pigs. All animal care and experimental procedures were approved by the Institutional Animal Care and Use Committee (IACUC) of the Cleveland Clinic.

Animals were sedated with xylazine and anesthesia was induced and maintained with isoflurane. Animals were placed supine to access the abdomen and anus. Sensors were calibrated before insertion into the colon through a speculum to distances of 10-50 cm.

Results

A. Bench Top Test Results

Color and IR sensors successfully detected the contraction of the phantom due to the proximity of the phantom wall to the sensors. They were able to distinguish between the gas and liquid materials. However, in solid material tests they were blocked and could not provide further data (FIG. 6).

The pressure sensor is capable of detecting pressure changes due to squeezing the phantom and increasing volume of the stools. Conductivity and capacitance correlated with stool volume.

B. In Vivo Test Results

In the first experiment, color and IR sensors were blocked by stool and were not sensitive to colon contraction or stool volume changes. This effect was expected from bench top testing. Therefore, the sensors were disregarded for further consideration in the later experiments.

Figure 7:
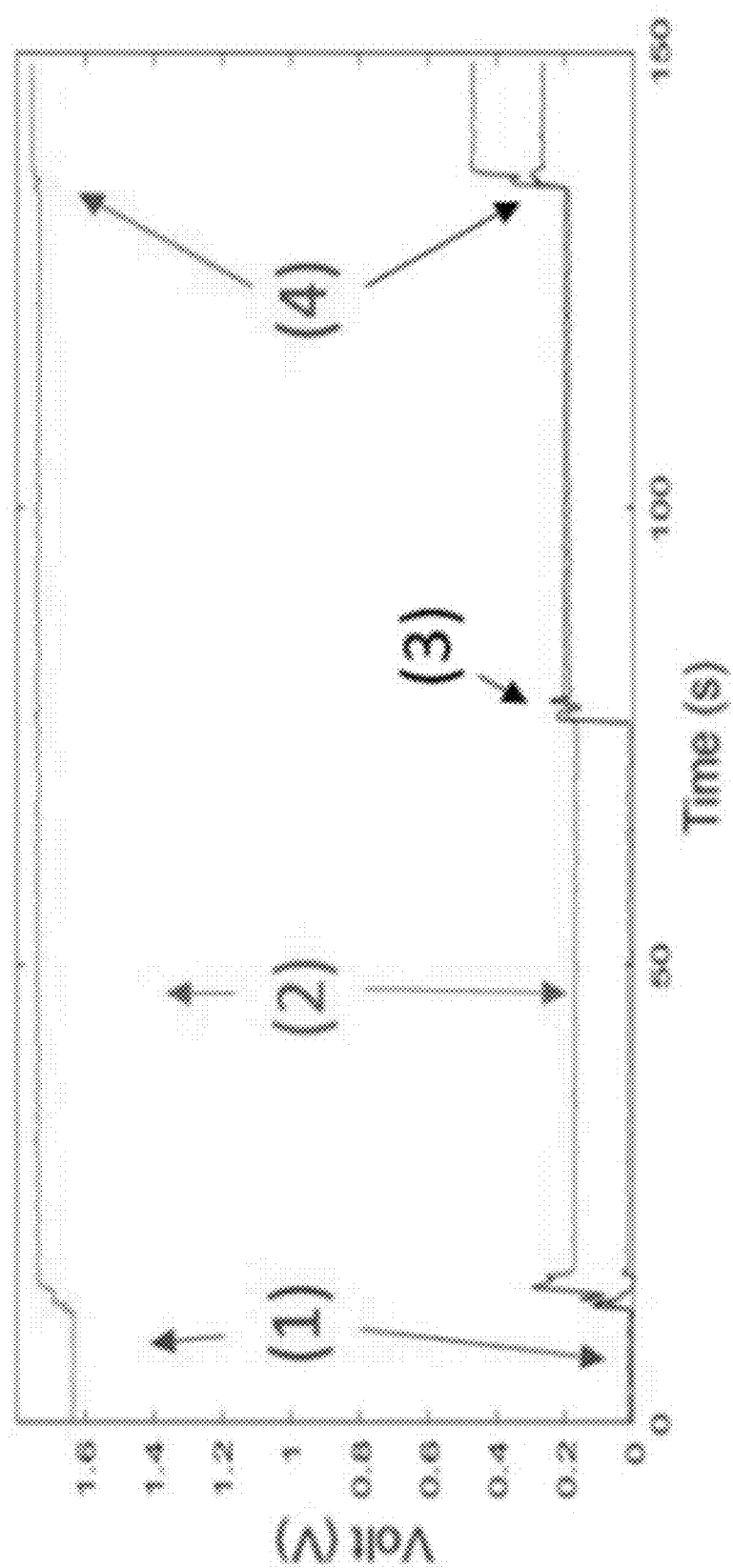
FIG. 7 is a graph depicting conductivity sensor response to stool volume change. 1) Only CA1 and A (FIG. 3) are covered with stool. 2) CA2 also covered. 3) Adding more stool to cover CA1, CA2, CA3 and A. 4) Adding more stool to increase the total volume of the stool.
Figure 8:
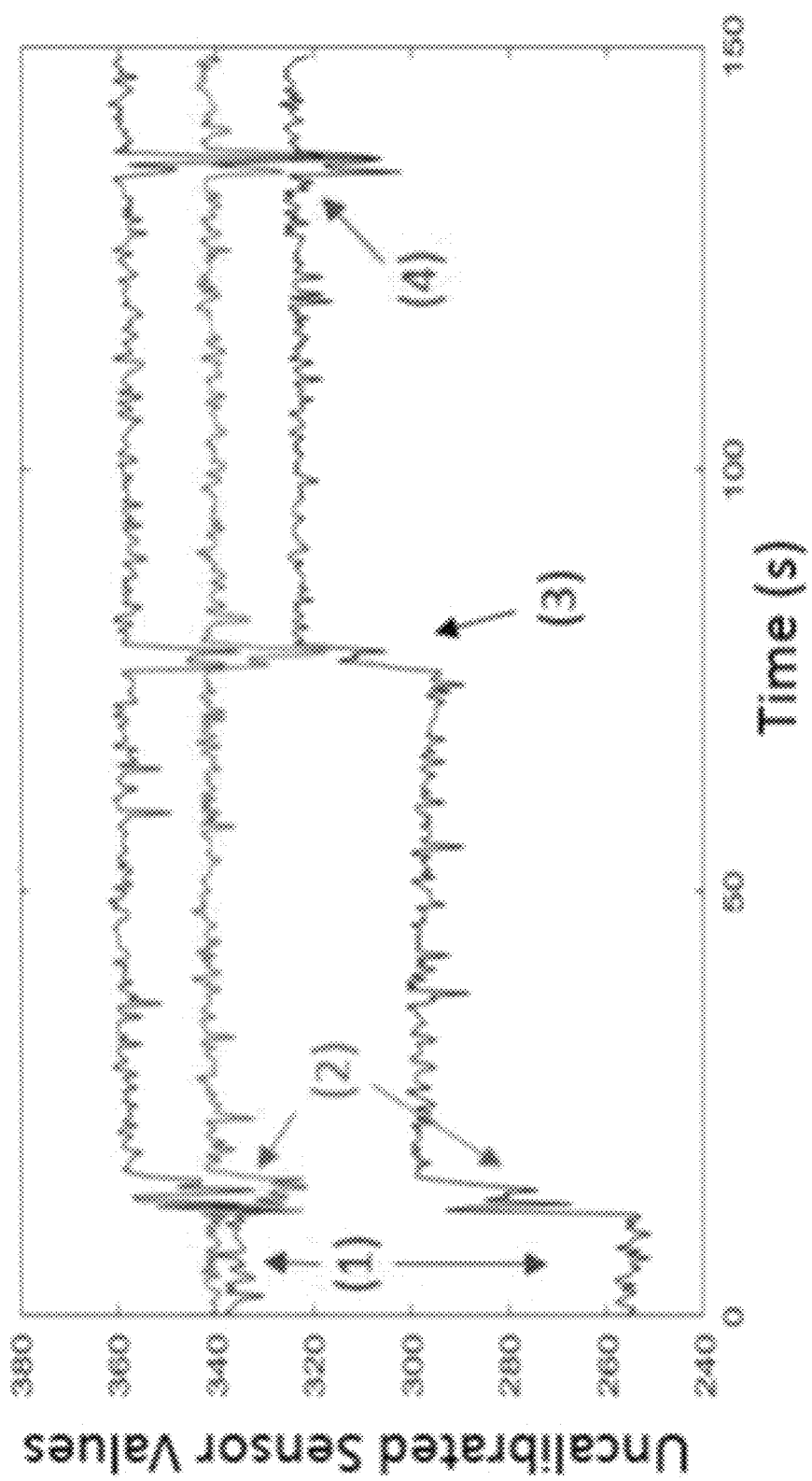
FIG. 8 is a graph depicting capacitive sensor capability in stool appearance detection. 1) Only CA1 and A are covered with stool. 2) Adding more stool to cover CA1, CA2, and A. 3) Adding more stool to cover CA1, CA2, CA3 and A. 4) Adding more stool to increase the total volume.
Figure 9:
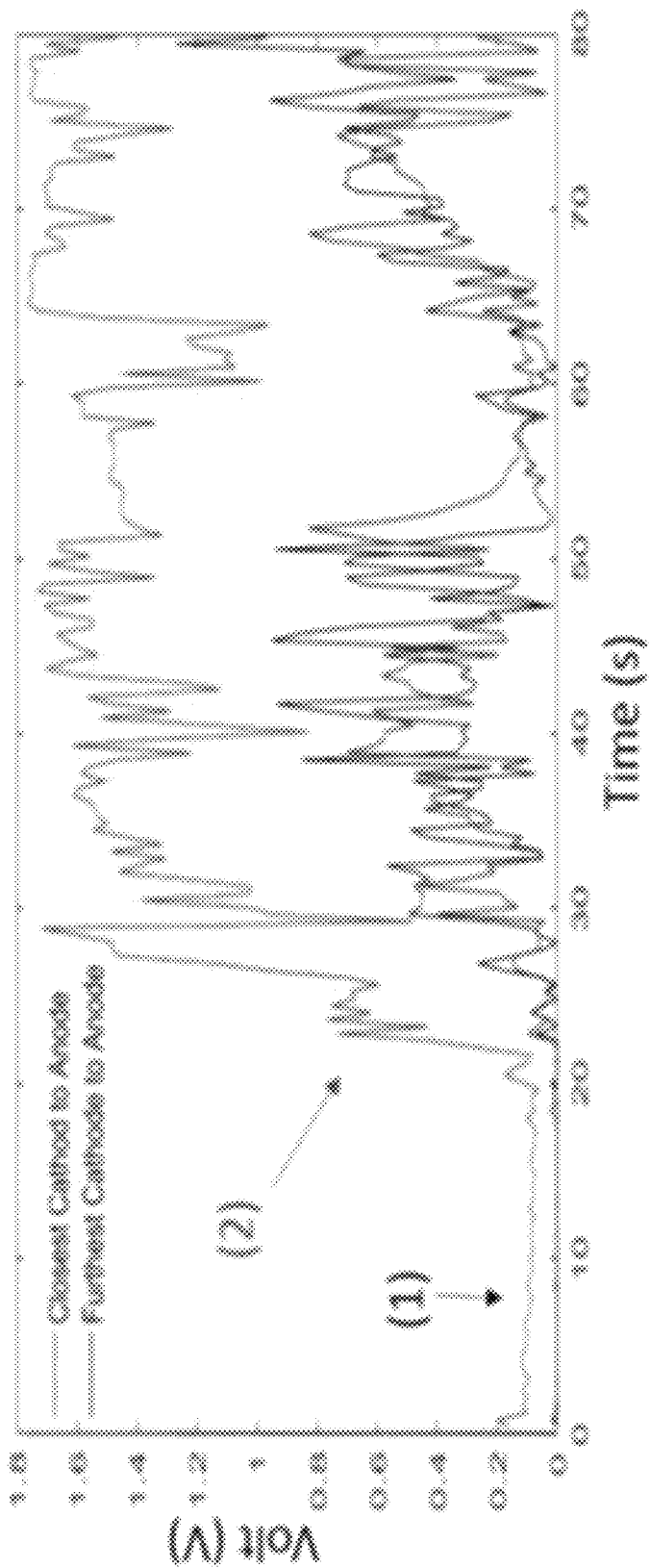
FIG. 9 is a graph depicting conductivity sensor capability in contraction detection. 1) No contraction. 2) Simulated contractions start.
Figure 10:
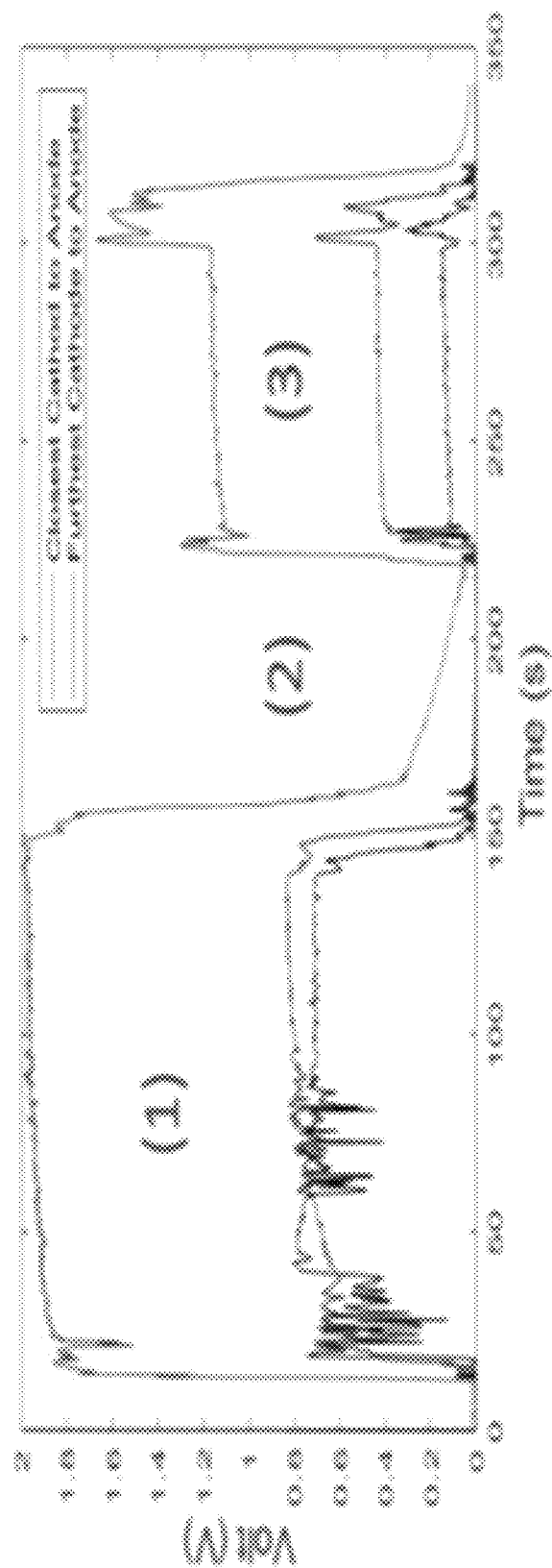
FIG. 10 is a graph depicting conductivity sensor differentiation between stool volume and gas. 1) Sensor inserted into the rectum while it is full with stool. 2) Sensor was taken out of the rectum. 3) Sensor was inserted back to the rectum with lower volume of stool.
Figure 11:
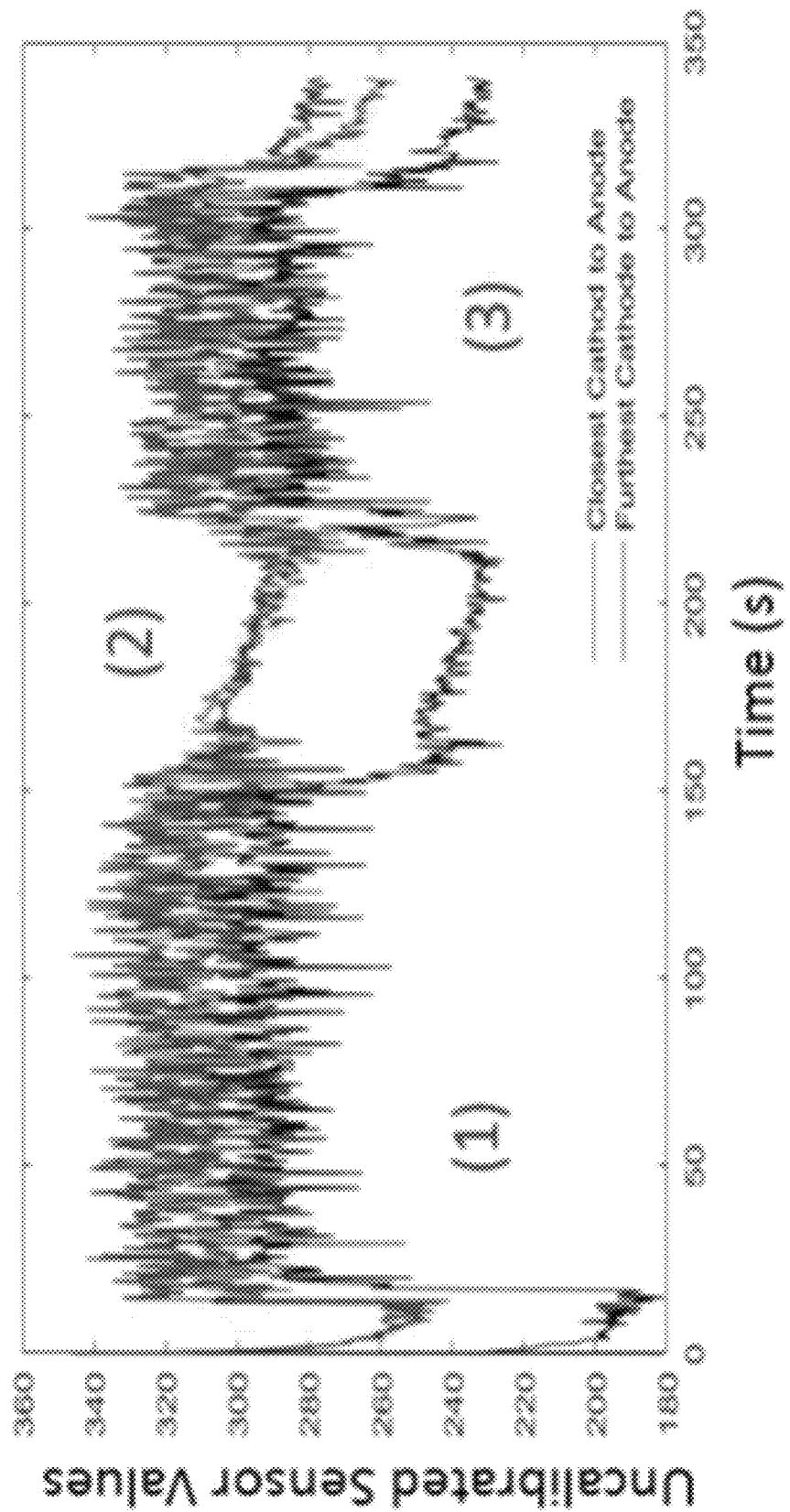
FIG. 11 is a graph depicting in vivo capacitive sensor measurements. 1) Sensor inserted into the rectum, full of stool. 2) Sensor removed from rectum. 3) Sensor was reinserted into the rectum with lower volume of stool.

Conductivity and capacitive sensors were initially tested by putting stool on the closest electrodes (~1.65 V at FIG. 7). More stool was then added to cover the second electrode. The same trend was continued for covering the third electrode with stool (FIGS. 7 & 8). As each electrode came in contact with stool, a monotonic increase in conductivity was seen. When all of the electrodes were covered with stool, adding more stool showed further shifts in the conductivity measurement (FIG. 7, 150 s). Therefore, conductivity measurement is feasible for volume estimation of the stool inside the colon. Although capacitive sensing was able to detect the presence of stool over the sensor and some changes in volume, it was not sensitive to the volume changes after the gaps between the plates were totally filled with stool (FIG. 8). Next, the sensor was inserted in the rectum through the anus and by squeezing the abdomen, the stool was moved across the device. Conductivity measurements showed these simulated contractions (FIG. 9). After this, the sensor was inserted into the rectum with different volumes of stool (FIG. 10). The conductivity sensor detected the volume change inside the rectum; however, the capacitive sensor was not as sensitive, although it was able to distinguish between a full and an empty rectum (FIG. 11).

Figure 12:
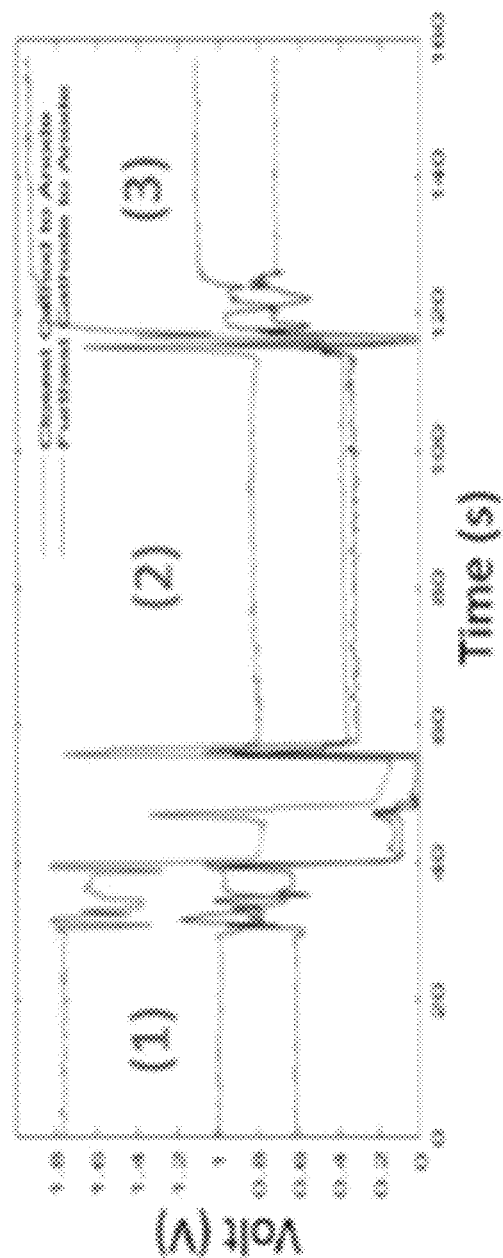
FIG. 12 is a graph depicting conductivity measurement of the colon wall vs the stool-filled colon lumen. 1) Sensors facing the stool. 2) Sensor board rotated to face the colon wall. 3) Sensor board rotated and facing the stool.

A laparotomy was then performed to access and visualize the colon. A small incision was created to insert the sensor board inside the colon. To test functionality of the sensors to discern between the colon wall and the stool, the sensor was tested under three conditions, including: (1) an empty colon with the electrodes facing into the colon wall; (2) an empty colon with the electrodes facing into the empty lumen; and (3) a colon filled with stool and the electrodes facing the stools (FIG. 12). The conductivity sensors were capable to discern between facing the colon wall and facing the stool.

Figure 13:
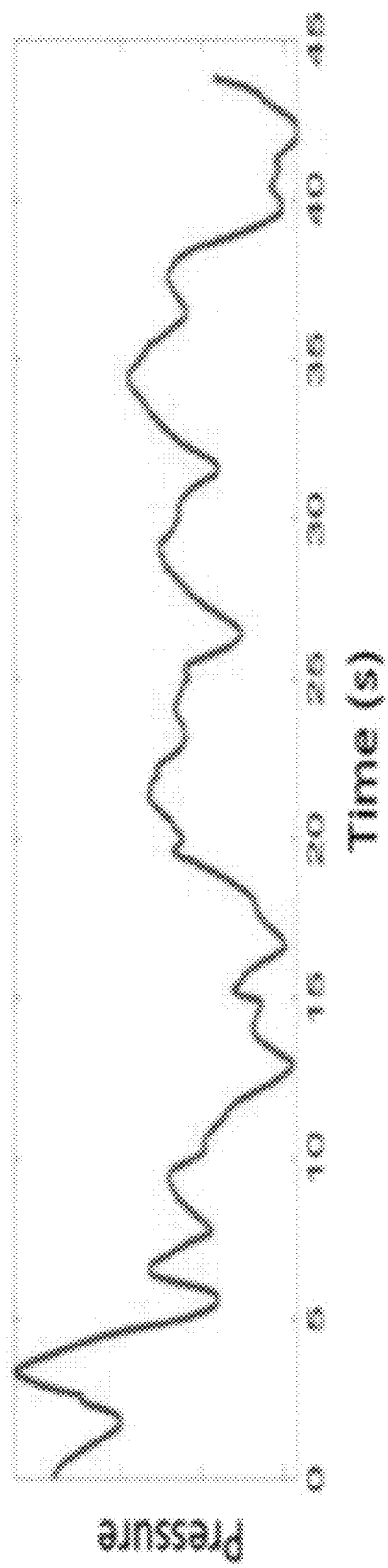
FIG. 13 is a graph depicting pressure sensor capability in detecting bowel fast waves.

The pressure sensor was tested by inserting the sensor board inside the colon and then muscle contractions were induced using electrical stimulation of the exterior colon surface (FIG. 13). Stimulation was administered every second in bursts of 20 pulses at 100 Hz at 40 mA and 0.5 ms pulse width.

From the above description, those skilled in the art will perceive improvements, changes and modifications. Such improvements, changes and modifications are within the skill of one in the art and are intended to be covered by the appended claims.

What is claimed is:

1. A sensing device comprising:
    a flexible printed circuit board comprising:
        at least one senor configured to record data related to bowel activity from a patient's colon; and
        a wireless transmitter configured to send the data from the patient's colon to an external device; and
    at least one mucosal clip configured to fix the sensor board to a wall of the patient's colon for a measurement period,
    wherein the flexible printed circuit board and/or the at least one mucosal clip are configured to be passed from the patient's colon after the measurement period through normal defecation.

2. The sensing device of claim 1, wherein the at least one sensor comprises at least one of a pressure sensor, a conductance sensor, and a capacitance sensor.

3. The sensing device of claim 1, wherein the at least one sensor comprises a pressure sensor, a conductance sensor, and a capacitance sensor,
    wherein the pressure sensor is located at a head of the printed circuit board,
    wherein metal mesh electrodes of the conductance sensor and/or the capacitance sensor are located at a tail of the printed circuit board.

4. The sensing device of claim 3, wherein the metal mesh electrodes comprise three cathodes (C1, C2, and C3) and one anode (A) located at different distances from each other.

5. The sensing device of claim 3, wherein the pressure sensor is configured to detect contraction of circular smooth muscle in the bowel.

6. The sensing device of claim 1, wherein the data related to bowel activity is used to determine at least one of a volume of the bowel, an aspect ratio of bowel contents, a shape of bowel contents, a geometry of bowel contents, a movement of bowel contents, a motility of bowel content, a material content of bowel content, a material form of bowel content, a pressure of bowel content, and/or bowel circumference.

7. The sensing device of claim 1, further comprising a u-shaped handle configured to attach the mucosal clip to the colon wall.

8. A method comprising:
    during a measurement period:
        recording, by at least one sensor located on a flexible printed circuit board of a sensing device anchored to a patient's colon by at least one mucosal clip, data related to bowel activity from the patient's colon;
        sending, by a wireless transmitter of the sensing device, the data from the patient's colon to an external device;
    after the measurement period:
        passing the flexible printed circuit board and/or the at least one mucosal clip from the patient's colon through normal defecation.

9. The method of claim 8, further comprising: before the measurement period, anchoring the flexible printed circuit board to the patient's colon by the at least one mucosal clip.

10. The method of claim 8, wherein the measurement period is at least 48 hours.

11. The method of claim 8, wherein the at least one mucosal clip dissolves after the measurement period to allow the flexible printed circuit board to be passed from the patient's colon through normal defecation.

* * * * *